United States Patent [19]

Sims et al.

[11] Patent Number: 4,854,725
[45] Date of Patent: Aug. 8, 1989

[54] MULTI-SENSOR STEAM QUALITY MONITORING MEANS AND METHOD

[75] Inventors: Jackie C. Sims; Donald J. Dowling; Theodore W. Nussbaum, all of Houston, Tex.

[73] Assignee: Texaco Inc., White Plains, N.Y.

[21] Appl. No.: 205,241

[22] Filed: Jun. 10, 1988

[51] Int. Cl.$^4$ ............................................. G01N 25/60
[52] U.S. Cl. ........................................ 374/42; 374/31; 73/29; 73/61 R; 324/61 P; 324/61 R
[58] Field of Search ................... 374/42, 31; 73/61 R, 73/61.1 R, 29; 324/61 P, 61 R, 60 C, 57 R

[56] References Cited

U.S. PATENT DOCUMENTS

| | | | |
|---|---|---|---|
| 3,253,606 | 5/1966 | Kuntz | 324/61 P |
| 3,450,988 | 6/1969 | Breen et al. | 324/61 P |
| 3,479,586 | 11/1969 | Perra | 324/57 R |
| 3,612,993 | 10/1971 | Tims | 324/57 R |
| 3,710,244 | 1/1973 | Rauchwerger | 324/61 P |
| 3,766,469 | 10/1973 | Nakane | 324/60 C |
| 3,786,349 | 1/1974 | Devenyi | 324/57 R |
| 3,970,925 | 6/1976 | Procter et al. | 324/60 R |
| 4,473,796 | 9/1984 | Nankivil | 324/60 C |
| 4,658,208 | 4/1987 | Lee et al. | 73/61 R |
| 4,769,593 | 9/1988 | Reed et al. | 374/42 |

FOREIGN PATENT DOCUMENTS 0082363 4/1987 Japan.

Primary Examiner—William A. Cuchlinski, Jr.
Assistant Examiner—Diego F. F. Gutierrez
Attorney, Agent, or Firm—Robert A. Kulason; James J. O'Loughlin; Ronald G. Gillespie

[57] ABSTRACT

A system of the present invention monitors the quality of steam flowing in a pipeline includes a test cell which is connected inline into the pipeline and has the steam flowing through it. A plurality of electrodes are located within the test cell and cooperate with the test cell to provide capacitance signals corresponding to capacitances of the steam passing between the electrodes and the test cell. The electrodes have different spacings between them and an interior wall of the test cell. A sensor senses the temperature of the steam flowing through the test cell and provides a temperature signal corresponding to the sensed temperature. Another sensor senses the pressure of the steam and provides a pressure signal corresponding to the sensed pressure. Circuitry connected to the test cell, to all the electrodes, to the temperature sensor and to the pressure sensor measures the quality of the steam in accordance with the temperature signal, the pressure signal and one of the capacitance signals.

11 Claims, 2 Drawing Sheets

MULTI-SENSOR STEAM QUALITY MONITORING MEANS AND METHOD

BACKGROUND OF THE INVENTION

FIELD OF THE INVENTION

The present invention relates to monitors and monitoring methods in general and, more particularly, to steam quality monitoring means and methods.

SUMMARY OF THE INVENTION

A system of the present invention which monitors the quality of steam flowing in a pipeline includes a test cell which is connected inline into the pipeline and has the steam flowing through it. A plurality of electrodes are located within the test cell and cooperate with the test cell to provide capacitance signals corresponding to capacitances of the steam passing between the electrodes and the test cell. The electrodes have different spacings between them and an interior wall of the test cell. A sensor senses the temperature of the steam flowing through the test cell and provides a temperature signal corresponding to the sensed temperature. Another sensor senses the pressure of the steam and provides a pressure signal corresponding to the sensed pressure. Circuitry connected to the test cell, to all the electrodes, to the temperature sensor and to the pressure sensor measures the quality of the steam in accordance with the temperature signal, the pressure signal and one of the capacitance signals.

The objects and advantages of the invention will appear more fully hereinafter from a consideration of the detailed description which follows, taken together with the accompanying drawings, where in one embodiment of the invention is illustrated by way of example. It is to be expressly understood, however, that the drawings are for illustration purpose only and are not to be construed as defining the limits of the invention.

DESCRIPTION OF THE INVENTION

Figure 1:
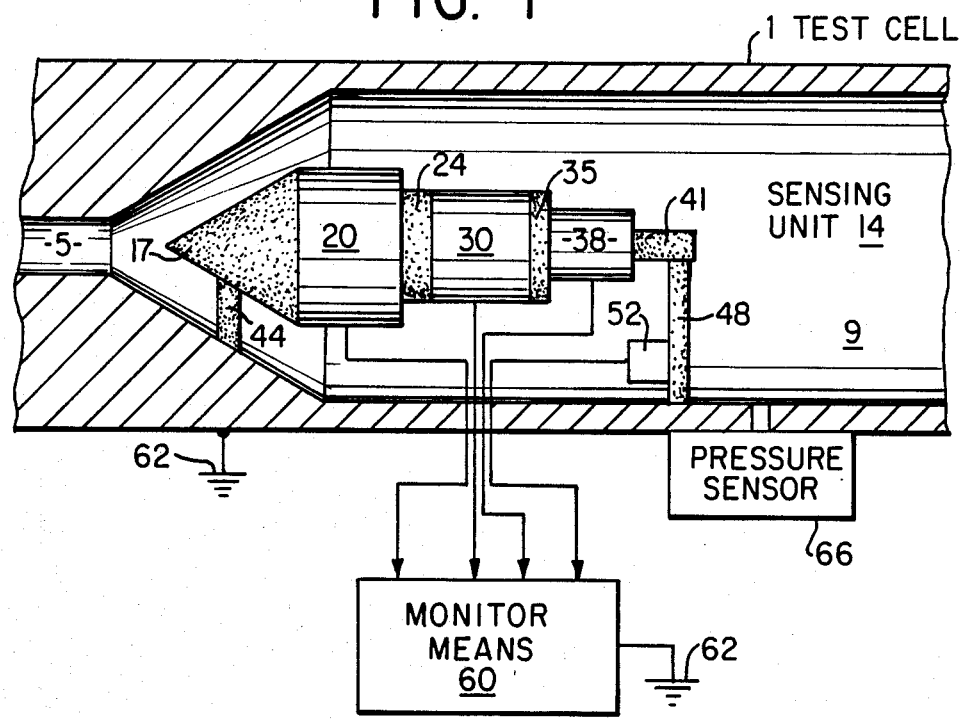
FIG. 1 shows a steam quality monitor constructed in accordance with the present invention.

Referring to FIG. 1, there is shown a test cell 1 mounted as part of a pipeline carrying steam. Test cell 1 has a constricted passageway 5 which enters an enlarged passageway 9 having the same diameter as the pipeline inner diameter. Mounted in passageway 9 is a sensing unit 14 which includes a cone 17 of non-conductive material having affixed thereto a circular electrode 20 having a first predetermined diameter. Affixed to electrode 20 is a circular insulator 24. Attached to insulator 24 is a second electrode 30 having a second predetermined diameter which is less than the diameter of electrode 20. Another insulator 35 is attached to electrode 30. A circular electrode 38 having a third predetermined diameter which is less than the diameter of electrode 30 is affixed to insulator 35 and has an insulator 41 attached to it. Support members 44 and 48 are attached to cone 17 and to insulator 41, respectively. Mounted on support member 48, but it can be mounted anywhere, is a temperature sensor 52 which senses the temperature of the steam and provides a corresponding signal T. Electrodes 20, 30 and 38 and temperature sensor 52 are electrically connected to monitor means 60. Test cell 1 and monitor means 60 are connected to ground 62. Also connected to test cell 1 is a pressure sensor 66, which is electrically connected to monitor means 60. Pressure sensor 66 senses the pressure of the steam and provides a corresponding signal P.

Figure 2:
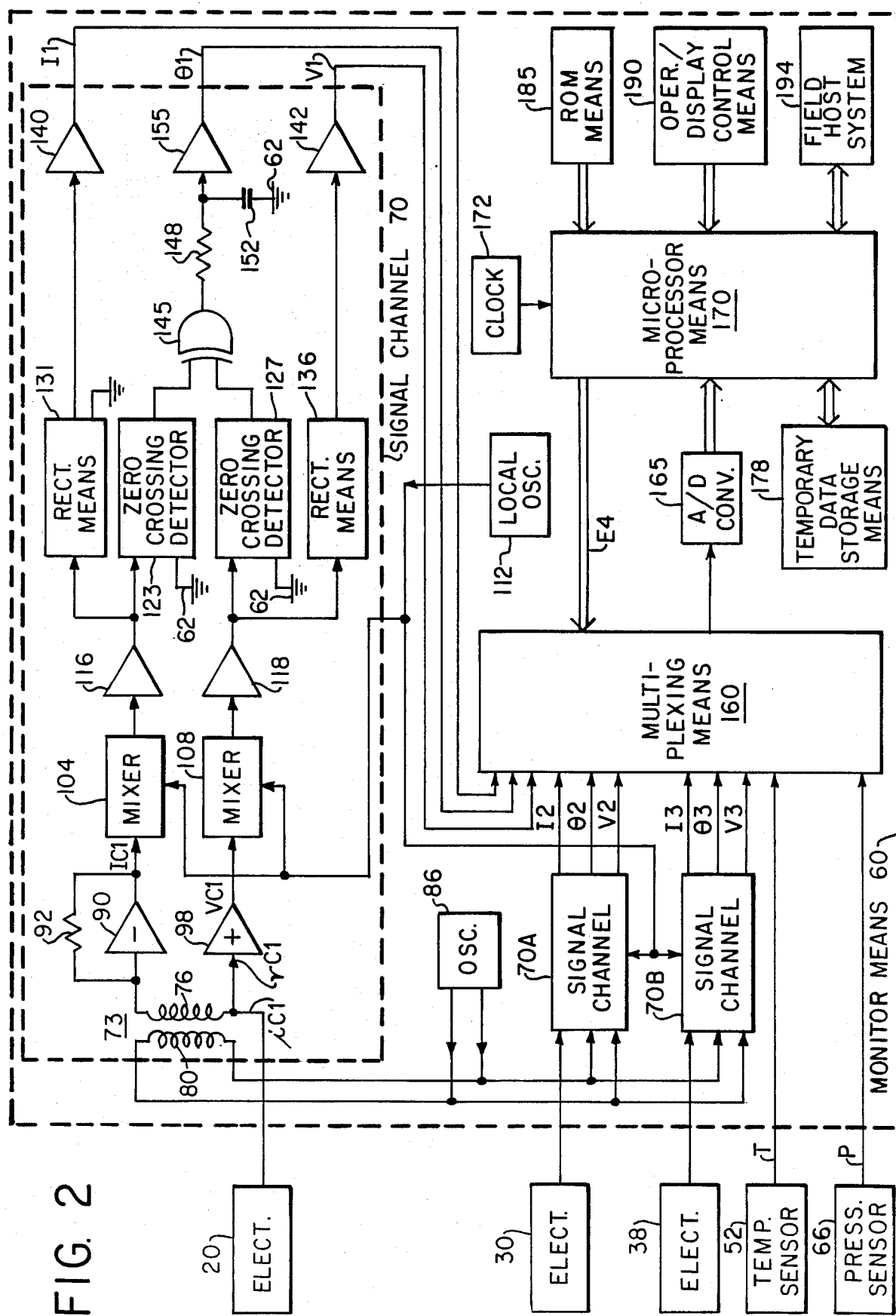
FIG. 2 is a simplified block diagram of the monitor means shown in FIG. 1.

With reference to FIG. 2, monitor means 60 includes three signal channels 70, 70A and 70B. Elements having a numeric alpha designation operate as the same elements having the same numeric designation but without an alpha suffix. Signal channel 70 includes a transformer 73 having a secondary winding 76, one end of which is connected to electrode 20. A primary winding 80 of transformer 73 receives a signal which has a frequency in the tens of megahertz from an oscillator 86; a preferred frequency is 20 MHz. A current iC1 is developed in the secondary winding 76 of transformer 73 from electrode 20 so that there exists a voltage vC1 between the connection of electrode 20 and winding 76 and ground 62. The other end of winding 76 is connected to an operational amplifier 90 having a feedback resistor 92 connected across it. Another operational amplifier 98 is connected to secondary winding 76 - electrode 20 connection.

The outputs of amplifiers 90 and 98 are provided to mixers 104 and 108, respectively, receiving a signal from a local oscillator 112 which is also provided to signal channel 70A and 70B. Mixers 104 and 108 provide intermediate frequency signals related to the signals provided by amplifiers 90 and 98, respectively, to IF amplifiers 116 and 118, respectively. A preferred frequency for the signal from the local oscillator 112 is 19.998 MHz so that the IF is 2 KHz.

The amplified signals provided by IF amplifiers 116 and 118 are provided to zero crossing detectors 123 and 127, respectively. Zero crossing detectors 123 and 127 are connected to ground 62. The outputs of IF amplifiers 116 and 118 are also applied to precision rectifiers means 131 and 136, respectively. The rectified signals provided by rectifiers 131 and 136 are provided to amplifiers 140 and 142, respectively.

Meanwhile, the outputs of zero crossing detectors 123 and 127 are provided to an exclusive OR gate 145 which provides its output through a filtering network, comprising a resistor 148 and a capacitor 152 connected to ground 62, to an output amplifier 155.

Output amplifiers 140, 142 and 155 provide signals I1, V1 and $\theta1$ respectively, to multiplexing means 160.

Signal channel 70A is connected to electrode 30, oscillator 86 and local oscillator 112 and operates as hereinbefore described for signal channel 70 to provide signals I2, V2 and $\theta2$ to multiplexing means 160.

Similarly, signal channel 70B is connected to electrode 38 and to oscillator 86 and local oscillator 112 and provides signals I3, V3 and $\theta3$ to multiplexing means 160. Temperature sensor 52 and pressure sensor 66 also sends signals T and P, respectively, to multiplexing means 160. The output of multiplexing means 160 is provided to an A to D converter 165 which provides corresponding digital signals to a microprocessor means 170 receiving timing pulses from a clock 172. Microprocessor means 170 also provides control signals E4 to multiplexing means 160 to control multiplexing means 160. Microprocessor means 170 derives the steam quality as hereinafter explained and provides data signals to temporary data storage means 178. Microprocessor means 170 receives data signals back from means 178 but receives control signals from read only memory means 185 and from operator/display control means 190. Microprocessor means also receives signals from a field host system 194 and also provides signals to field host system 194.

THEORY OF OPERATION

In order to determine the vapor/water fraction of the steam used in petroleum reservoir enhanced recovery floods, some monitors include capacitance devices used to sense the dielectric effects of the multiple fluids. As the vapor/water fraction varies in accordance with the steam quality, the resulting dielectric constant shift causes a detectable capacitive change in the sensor.

The determination of capacitance electronically is typically accomplished by the separation of the quadrature term from the change in complex impedance of the sensor. Stated mathematically:

$$Z = R - jX \tag{1}$$

where Z is the complex impedance, R is the energy loss term and the imaginary, j, or quadrature term, jX, is the reactance of the sensor capacitance.

Figure 3:
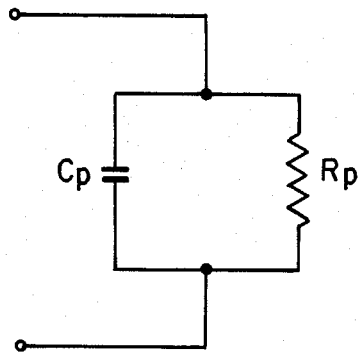
FIGS. 3 and 4 are schematics of equivalent circuits representing the steam being monitored.

The sensor impedance is modelled as a parallel combination of resistance, $R_p$, and capacitance $C_p$, as shown in FIG. 3. Because of the imperfection of any practical device or component the losses modelled as $R_p$ contribute to an overall dissipation of energy. This effect is labelled dissipation factor, D, and is expressed:

$$D = X_{cp}/R_p \text{ (For Parallel Circuit)} \tag{2a}$$

and $$D = R_s/X_{cs} \text{ (For Series Circuit)} \tag{2b}$$

where $X_{cp}$ is the capacitive reactance of $C_p$, and $X_{cs}$, that of $C_s$, in the series circuit $R_s$ and $X_{cs}$.

Figure 4:
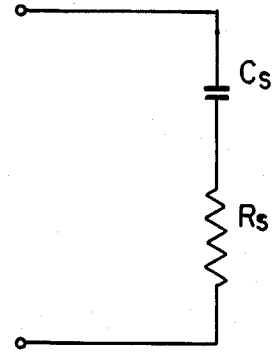

Electrical engineering theory permits the impedance, shown as a parallel $R_p$ and $C_p$ in FIG. 3, to also be modelled as a series $R_s$ and $C_s$ as shown in FIG. 4.

These two circuits are related by the dissipation factor, D, as:

$$R_s = (D^2(1+D^2)) R_p \tag{3}$$

$$C_s = (1+D^2) C_p \tag{4}$$

$$R_p = ((1+D^2)/D^2) R_s \tag{5}$$

$$C_p = (1/(1+D^2)) C_s \tag{6}$$

When evaluating external influences on the sensor (steam flow for example), the parallel model is most often used. The measuring instrumentation used to serve the sensor, however, generally treats the "unknown" connected to its input terminals as a series circuit. Consequently, the conversion accuracy from series to parallel or vice versa is strongly dependent on the resolution ability of the instrumentation in the determination of the in-phase and the quadrature components of the complex impedance, Z.

Equations 5 and 6 show the importance of the factor D in the ultimate determination of the sensor parallel equivalent.

It can be seen from Equation 2 that both the reactance and the loss terms affect the dissipation factor. In practice, however, the loss term $R_p$ has a greater negative influence on D due to the wide range of its values. Under conditions of moderate to low steam quality, (a very economical petroleum reservoir operating mode) it has been found that some field representative values of $R_p$ can cause large inaccuracies and in some cases data loss in the sensor measurements.

The excessive loss represented by such values of $R_p$ can be thought of in two ways.

a. As the steam quality decreases, the likelihood of several particles of water agglomerating or "stacking up" increases. If these "stacks" of water particles become large enough and sufficient in number, they can cause an ohmic path to form between the sensor capacitance plates. The resulting dissipation factor, D, rises substantially.

b. Additionally, when the steam is wet enough to have a highly conductive but dispersed mixture of vapor and water the displacement current between the sensor plates manifests itself as an equivalent low value of $R_p$ causing an excessive D.

In both cases described the result is severe degradation of the accuracy of the measuring instrumentation.

Again with reference to FIGS. 1 and 2, as indicated before, when "stacking" of the water particles is sufficiently large enough to bridge the sensor spacing an ohmic or resistance path occurs between the plates. The dimensions of a single stack is such that the overall conductivity in the total region between the plates is not radically altered. It is altered, however, when a large fraction of the sensing volume is filled with "stacks".

The three electrodes 20, 30 and 38 form a coaxial capacitor type sensor with test cell 1 with the annular spacing between electrodes 20, 30 and 38 and test cell 1 varying as a function of the diameters of electrodes 20, 30 and 38. Thus, the coaxial capacitor between electrode 20 and test cell 1 is more sensitive to "stacking" than is electrode 30 and test cell 1. The least sensitive obviously is electrode 38 and test cell 1.

Since all three signal channels 70, 70A and 70B operate in the same manner only signal channel 70's operation will be discussed herein. Electrode 20 causes a current to flow in secondary winding 76 of transformer 73 iC1 which develops a voltage vC1 at the common connection between winding 76 and electrode 20 and amplifier 98 with respect to ground 62. Amplifiers 90 and 98 function as a current sensor and a voltage sensor, respectively and it should be noted that there is a phase difference occurring due to the capacitance between electrode 20 and test cell 1 so that the current output of amplifier 90 leads the voltage output of amplifier 98 by a phase difference $\theta$C1. Mixer 104 and IF amplifier 116 as well as mixer 108 and IF amplifier 118, function as frequency converters. The output of IF amplifier 116 is rectified to a DC current and amplified by amplifier 140 and as noted amplifier 140 provides the current as I1. Similarly the output of IF amplifier 118 is rectified and provided to amplifier 142 which provides a voltage V1.

The cooperation of zero crossing detectors 123 and 127 with exclusive OR gate 145, the filtering network of resistor 148 and capacitor 152, results in a signal related to the phase difference $\theta$1 between the current iC1 and the voltage vC1. The phase difference signal is provided to the amplifier 155 which provides the phase difference signal $\theta$1.

Calculation of complex impedance, $Zx = Rx - jXcx$, is done by the microprocessor means 170 on the equivalent digital signals representing Icx, Vcx and $\theta$cx in the following manner:

7. $/Z_x/ = (Vcx/Icx) * k$ where k is a calibration constant obtained using a known standard impedance. In the present description Icx, Vcx and $\theta$cx are represented by signals I1, V1 and $\theta$1; I2, V2 and $\theta$2; or I3, V3 and $\theta$3, respectively.

Further

8. $Rx = /Z_x/ * \cos \theta cx$ where $R_x$ is the resistive term of the impedance $Z_x$ and 9. $Xcx = /Z_x/ * \sin \theta cx$ where Xcx is the reactive term of impedance $Z_x$.

Rpx, calculated from each of the three electrodes 20, 30 and 38 and ground 62, is then used to determine which electrode and ground 62 will produce the most accurate Cx for steam quality calculation. Since the value of Rx can vary from location to location depending largely on the steam generator feedwater conductivity, the switch-over values of Rx would typically be determined empirically at installation and entered into temporary data storage means 178.

Xcx is used to obtain the measured capacitance C from equation 11:

$$C = \tfrac{1}{2}\pi f_o Xcx \qquad (10)$$

where $f_o$ is the frequency of the signal provided by oscillator 86.

With this value of C the equation 12 following which is programmed in the ROM means 185 can be solved by the microprocessor means 170 to yield X, steam quality as shown by:

$$X = (C^n - C_v n K_w^n)/[(1 - P_w/P_v)C^n - C_v^n K_w n + (P_w/P_v)C_v^n K_v^n] \qquad (11)$$

where C is sensed capacitance, $C_V$ is the capacitance of vapor, $P_v$ is the corrected density of vapor, $P_w$ is the corrected density of water, $K_V$ is the dielectric constant of vapor, $K_W$ is the dielectric constant of the water at the sensed temperature, and n is an exponent related to the geometry of the steam water particles. It should be noted that $P_v$ and $P_w$ are derived from specific volume data of steam at the steam's temperature.

Equation 11 was derived in a copending application Ser. No. 125507, filed Nov. 25, 1987. Microprocessing means 170 can provide for display and recording signals relating to all nine signals from the three signal channels 70, 70A and 70B, temperature and pressure, and further, should stacking occur selectively use channels 70A and/or 70B to determine the steam quality. Thus, the present invention as hereinbefore described in effect extends the range of usage of a capacitance type sensor over the quality range of the steam.

What is claimed is:

1. A system for monitoring the quality of steam flowing in a pipeline comprising:
    a test cell means, configured for in-line connections in the pipeline, for having the steam flow through the test cell means,
    a plurality of electrode means located within the test cell means for cooperating with the test cell means to provide capacitance signals corresponding to the capacitance of the steam passing between the electrode means and the test cell means, the electrode means being spaced different distances from an interior wall of the test cell means,
    temperature sensing means for sensing the temperature of the flowing steam and providing a temperature signal corresponding to the sensed temperature,
    pressure sensing means for sensing the pressure of the flowing steam and providing a pressure signal representative of the sensed pressure, and
    measuring means connecting to the test cell means, to all the electrode means, to the temperature sensing means and to the pressure sensing means for measuring the quality of the steam in accordance with the temperature signal, the pressure signal and at least one of the capacitance signals.

2. A system as described in claim 1 in which the measuring means includes:
    oscillator means for providing a signal at a predetermined frequency,
    local oscillator means for providing a signal at a second predetermined frequency,
    a plurality of generator means, each generator means being connected to the oscillator means, to the local oscillator means, to a corresponding electrode means and to the test cell for generating a current signal and a voltage signal for the electrode means in accordance with the capacitance signal provided by the electrode means and the signal provided by the oscillator means,
    a plurality of phase detector means, each phase detector means being connected to a corresponding generator means for providing a phase difference signal corresponding to the phase difference between the current signal and the voltage signal from the generator means, and
    deriving means connected to all the generator means, to all the phase detector means, to the temperature sensing means and to the pressure sensing means for deriving the steam's quality in accordance with the current signal, the voltage signal and the phase difference signal from at least one of the generator means and the temperature and pressure signals.

3. A system as described in claim 2 in which each generator means includes:
    transformer means having a first winding connected to the oscillator means and a second winding having one end connected to a corresponding electrode means for developing a current in the second winding in accordance with the capacitance signal from the electrode means and the signal from the oscillator means,
    a buffer means connected to the one end of the second winding of the transformer means for providing a signal representative of a voltage between the one end of the second winding and the test cell means,
    converter means connected to another end of the second winding of the transformer means for providing a voltage corresponding to the current flowing in the second winding,
    first and second mixer means connected to the buffer means and to the converter means, respectively, and connected to the local oscillator means for providing the voltage signal and the current signal, respectively.

4. A system as described in claim 3 in which each phase detector means includes:
    first and second zero crossing detector means connected to the first and second mixer means, respectively, an exclusive OR gate connected to the first and second zero crossing detector means for providing a signal corresponding to the phase difference between the current signal and the voltage signal, and means connected to the first and second mixer means for converting the signals from the first and second mixer means to direct current signals which are provided as the voltage signal and the current signal, respectively.

5. A system as described in claim 4 in which there are three electrode means in the plurality of electrode means.

6. A system as described in claim 5 in which the three electrode means are mounted within the test cell as one assembly including:
    a cone of insulating material,
    a first electrode affixed to the cone having a first diameter,
    a first circular insulator, affixed to the first
    a second electrode affixed to the first circular insulator having a second diameter which is less than the diameter of the first electrode,
    a second circular insulator affixed to the second electrode, and
    a third electrode affixed to the third insulator and having a third diameter which is less than the second electrode's diameter, and
    support members affixed to the third electrode and to the nose cone for maintaining the electrodes in spatial relationship to the test cell.

7. A method of monitoring the quality of steam flowing in a pipeline comprising the steps of:
    connecting a test cell in-line with the pipeline,
    having the steam flow through the test cell,
    spacing a plurality of electrodes within the test cell and at different distances from an interior wall of the test cell for cooperation with the test cell to provide capacitance signals corresponding to the capacitance of the steam passing between the electrodes and the test cell interior wall,
    sensing the temperature of the flowing steam,
    providing a temperature signal corresponding to the sensed temperature,
    sensing the pressure of the flowing steam
    providing a pressure signal representative of the sensed pressure, and
    measuring the quality of the steam in accordance with the temperature signal, the pressure signal and at least one of the capacitance signals.

8. A method as described in claim 7 in which the measuring step includes:
    providing a signal at a predetermined frequency with an oscillator,
    providing a local oscillator signal at a second predetermined frequency with a local oscillator,
    generating a current signal and a voltage signal for each capacitance signal in accordance with the capacitance signals provided by the electrodes and the signal provided by the oscillator,
    providing a phase difference signal for each set of voltage and current signals, each phase difference signal corresponding to the phase difference between a current signal and its associated voltage signal, and
    deriving the steam's quality in accordance with at least one set of current and voltage signals, a corresponding phase difference signal and the temperature and pressure signals.

9. A method as described in claim 8 in which each generating step includes:
    connecting a first winding of a transformer to the oscillator,
    developing a current in a second winding of the transformer in accordance with the capacitance signal from the electrode and the signal from the oscillator,
    providing a signal representative of a voltage between the one end of the second winding of the transformer and the test cell,
    providing a voltage corresponding to the current flowing in the second winding of the transformer, and
    providing the voltage signal and the current signal in accordance with the signal representative of the voltage between the test cell and the one end of the second winding of the transformer and of the signal corresponding to the current flowing in the second winding, respectively.

10. A method as described in claim 9 in which the phase signal step includes:
    detecting the zero crossings of the voltage signal and the current signal,
    providing zero crossing signals in accordance with the zero crossing detecting,
    providing a signal corresponding to the phase difference between the current signal and the voltage signal in accordance with the zero crossing signals, and
    converting the voltage and current signals to direct current signals.

11. A method as described in claim 10 in which there are three electrodes in the plurality of electrodes.

* * * * *